United States Patent [19]

Hajek et al.

[11] Patent Number: 4,642,344
[45] Date of Patent: Feb. 10, 1987

[54] POLYAMINES

[75] Inventors: Manfred Hajek; Herbert Salzburg, both of Cologne; Heinz Ziemann, Leichlingen, all of Fed. Rep. of Germany

[73] Assignee: Bayer Aktiengesellschaft, Leverkusen, Fed. Rep. of Germany

[21] Appl. No.: 690,445

[22] Filed: Jan. 11, 1985

[30] Foreign Application Priority Data

Jan. 19, 1984 [DE] Fed. Rep. of Germany ....... 3401675

[51] Int. Cl.$^4$ ............................................. C07D 251/70
[52] U.S. Cl. ..................................... 544/196; 544/197
[58] Field of Search ................................ 544/196, 197

[56] References Cited

U.S. PATENT DOCUMENTS

| 3,669,964 | 6/1972 | D'Alelio | 544/197 |
| 3,755,322 | 8/1973 | Winter et al. | 544/197 |
| 3,963,714 | 6/1976 | Gerandas et al. | 544/197 |
| 3,988,292 | 10/1976 | Moriga et al. | 544/197 |
| 3,988,337 | 10/1976 | Narayan et al. | 260/249.6 |
| 4,514,399 | 4/1985 | Regnier et al. | 544/196 |

FOREIGN PATENT DOCUMENTS

| 2653834 | 6/1978 | Fed. Rep. of Germany . |
| 49-39272 | 10/1974 | Japan | 544/196 |

OTHER PUBLICATIONS

Chemical Abstracts, No. 115093s, vol. 88, No. 17, Apr. 24, 1978.
Chemical Abstracts, No. 145542j, vol. 87, No. 19, Nov. 7, 1977.
Greenfield, Eng. Chem. Products, Res. Develop., 6, 142 (1967).
Bruson, Org. Reactions, 5, 79–155 (1949).
Kaiser et al, J. Amer. Chem. Soc., 73, 2984 (1951).

Primary Examiner—John M. Ford
Attorney, Agent, or Firm—Gene Harsh; Joseph C. Gil; Thomas W. Roy

[57] ABSTRACT

The present invention relates to new polyamines corresponding to the formula

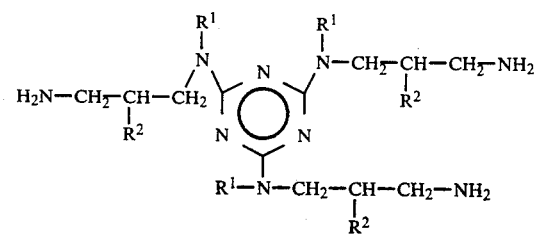

in which
$R^1$ represents an alkyl, cycloalkyl or aryl group and
$R^2$ represents hydrogen or an alkyl group.

The present invention is also directed to a process for the preparation of these amines by hydrogenating the corresponding trinitriles.

3 Claims, No Drawings

POLYAMINES

BACKGROUND OF THE INVENTION

1. Field of the Invention

The present invention is directed to new polyamines, in particular, triamines and a process for their preparation by hydrogenating trinitrile precursors.

2. Description of the Prior Art

The possibility of satisfactory preparation of the compounds according to the invention by the process according to the invention is surprising since on the one hand it was known from Ing. Eng. Chem. Prod. Res. Develop. 6, 142 (1967) that the hydrogenation of trinitriles must be expected to be accompanied by the formation of oligomers due to condensation so that the preparation of uniform compounds is generally not possible and, on the other hand, it was also known that triazines are powerful catalyst poisons and the hydrogenation of triazine derivatives would therefore be difficult (see e.g. M. Freifelder: "Practical Catalytic Hydrogenation" page 622, Wiley Interscience, Wiley and Sons).

SUMMARY OF THE INVENTION

The present invention relates to new polyamines corresponding to the formula

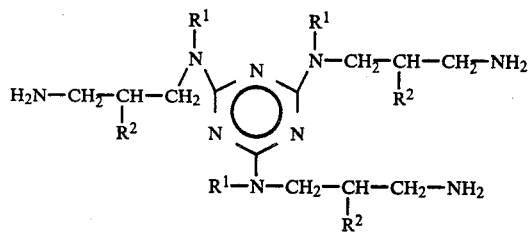

in which
$R^1$ represents an alkyl, cycloalkyl or aryl group and $R^2$ represents hydrogen or an alkyl group.

The present invention also relates to a process for the preparation of the polyamines according to the invention, characterized in that trinitriles corresponding to the formula

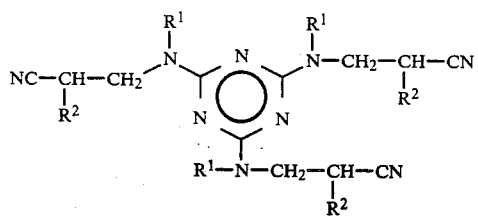

wherein $R^1$ and $R^2$ have the meaning indicated above, are catalytically hydrogenated in known manner with conversion of nitrile groups into amino groups.

DETAILED DESCRIPTION OF THE INVENTION

The trinitriles to be used in the process according to this invention may be obtained, for example, by the known condensation reaction of cyanuric chloride with addition products of primary amines and acrylonitrile or 2-substituted acrylonitriles such as methacrylonitrile or by the addition of such olefinically unsaturated nitriles to N,N',N''-trisubstituted melamines.

The syntheses are represented by the following scheme:

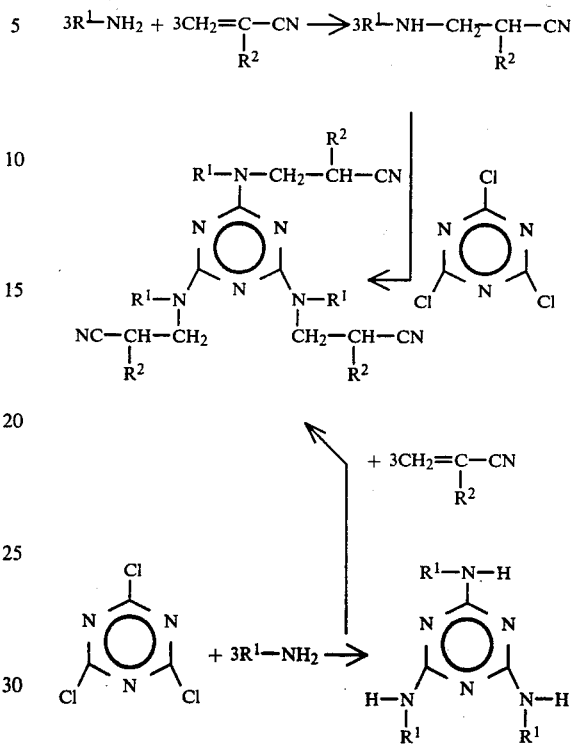

Thus, for example, the addition of the primary amine to the optionally 2-substituted acrylonitrile may be carried out using stoichiometric quantities of the reactants at about 20° to 120° C. in the presence of suitable solvents such as toluene, dioxane or acetonitrile or solvent-free by the process described in Org. Reactions 5, 79–135 (1949). Reaction of the addition product with cyanuric chloride may then be carried out, for example, using stoichiometric quantities of the reactants at about 0° to 120° C. in suitable solvents such as water, dioxane, acetone or toluene, by a method analogous to that described in J. Am. Chem. Soc. 73, 2984 (1951). The following compounds are examples of preferred starting materials for the preparation of trinitriles by this method:

(a) Primary alkyl, cycloalkyl or arylamines, in particular alkylamines having 1 to 6 carbon atoms, e.g. methylamine, n-propylamine, isopropylamine, n-butylamine, isobutylamine, n-hexylamine, cyclohexylamine or aniline. Alkylamines of the above-mentioned type having 1 to 4 carbon atoms are particularly preferred.

(b) Acrylonitrile optionally alkyl substituted in the 2-position, in particular, acrylonitrile or methacrylonitrile.

(c) Cyanuric chloride.

To carry out the process according to the invention, the trinitriles are hydrogenated with hydrogen by known methods in the presence of ammonia in an autoclave in a polar solvent having a dielectric constant >7 (DIN 53 483), such as methanol, ethanol, water, aqueous acetic acid or mixtures, e.g. of the solvents mentioned above. The temperature should be within the range of about 60° to 180° C., preferably about 85° to 160° C. The reaction proceeds particularly smoothly at temperatures from about 100° to 150° C.

A pressure of from about 100 to 200 bar, in particular from about 145 to 180 bar, is preferably maintained in the autoclave during hydrogenation.

Hydrogenation is preferably carried out in the presence of a catalyst. Raney nickel and Raney cobalt are particularly suitable, but nickel-iron or cobalt-iron catalysts as well as catalysts from the platinum group are also suitable.

In accordance with the above comments regarding suitable starting materials, the preferred triamines according to this invention are those corresponding to the above general formula in which $R^1$ represents an alkyl group having 1 to 6 carbon atoms, in particular 1 to 4 carbon atoms, a cyclohexyl group or a phenyl group, and $R^2$ represents hydrogen or a methyl group.

The triamines according to the invention are obtained in liquid form and in high yields and are recovered by removal of the catalyst by filtration and evaporation of the solvent. Distillation under high vacuum provides exceptionally pure products, as does also the thermal decomposition of the carbonic acid salt.

The new triamines according to this invention represent inter alia valuable cross-linking agents for epoxide resins or for compounds containing isocyanate groups. The new polyamines are also suitable for use as starting materials in the production of polyamide products.

The invention is further illustrated but is not intended to be limited by the following examples in which all parts and percentages are by weight unless otherwise specified.

EXAMPLES

EXAMPLE 1

(a) Preparation of the starting material N,N',N''-tris-(2-cyanoethyl)-N,N',N''-trimethylmelamine 240 g (10 mol) of freshly distilled 3-(methylamino)-propionic acid nitrile in 2 liters of ethanol/water (volumetric ratio 1:1) were adjusted to a temperature of $-5°$ C. to $-10°$ C. with stirring together with 500 g (5 mol) of sodium carbonate, and a solution of 555 g (3 mol) of cyanuric chloride in 2 liters of acetone was added dropwise at this temperature. After an initial exothermic reaction, the solution of cyanuric chloride in acetone was added more rapidly but still dropwise, and the reaction mixture was then stirred for 3 hours at about 0° to 5° C. and then for 8 to 10 hours while slowly heating to 60° C. After the end of the reaction, the reaction mixture was cooled to about 5° to 10° C. and the precipitate was filtered off.

After washing three times with 200 ml portions of water and then drying, 905 g (92.3%) of product, melting point 173° C., were obtained.

(b) N,N',N''-tris-(3-aminopropyl)-N,N',N''-trimethylmelamine 100 g of tris-nitrile (0.31 mol) from Example 1(a) in 500 ml of water and 500 ml of methanol were heated to 130° C. with 600 ml of liquid ammonia and 40 g of Raney nickel, and hydrogen was forced in under a pressure of 145 bar. After 3.5 hours, the mixture was freed from catalyst by filtration after cooling and release of pressure. The catalyst may be used again for the reaction. If necessary, the solution of product is decolorized with active charcoal and then concentrated by evaporation at 100° C./25 mm Hg.

94.2 g of colorless syrup (89.8%) were obtained. Exceptionally pure tris-amine was obtained when the precipitated crude syrup was distilled at 0.1 mm/250° C. The carbonic acid salt had a melting point of 92° C. (elimination of $CO_2$).

EXAMPLE 2

100 g of N,N',N''-tris-(2-methyl-2-cyanoethyl)-N,N',N''-trimethyl-melamine (0.27 mol) were hydrogenated as described in Example 1(b). 90 g (87.8%) of N,N',N''-tris-(2-methyl-3-aminopropyl)-N,N',N''-trimethylmelamine were obtained as colorless syrup.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyamine corresponding to the formula

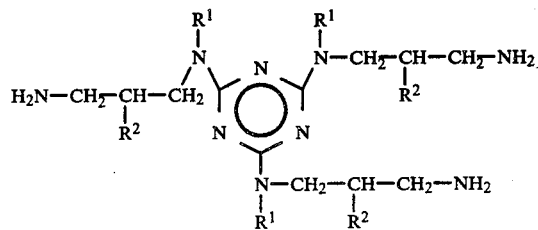

wherein $R^1$ represents an alkyl group having 1 to 6 carbon atoms, a cyclohexyl group or a phenyl group and $R^2$ represents hydrogen or a methyl group.

2. The polyamine of claim 1, wherein $R^1$ represents an alkyl group having 1 to 4 carbon atoms.

3. The polyamine of claim 1, wherein $R^1$ represents a methyl group.

* * * * *